(12) United States Patent
Karamanoglu et al.

(10) Patent No.: US 8,702,604 B2
(45) Date of Patent: Apr. 22, 2014

(54) DETECTION OF WAVEFORM ARTIFACT

(75) Inventors: Mustafa Karamanoglu, Fridley, MN (US); Karen J. Kleckner, New Brighton, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 384 days.

(21) Appl. No.: 13/017,307

(22) Filed: Jan. 31, 2011

(65) Prior Publication Data

US 2012/0197088 A1 Aug. 2, 2012

(51) Int. Cl.
*A61B 5/00* (2006.01)
*G06F 19/00* (2011.01)

(52) U.S. Cl.
CPC .................. *G06F 19/3406* (2013.01)
USPC .......................... 600/300; 600/485

(58) Field of Classification Search
USPC .................. 600/300, 301, 485, 500
See application file for complete search history.

(56) References Cited

U.S. PATENT DOCUMENTS

| | | | | |
|---|---|---|---|---|
| 4,105,023 | A | * | 8/1978 | Marchese et al. ............. 600/510 |
| 4,911,167 | A | * | 3/1990 | Corenman et al. ............ 600/324 |
| 5,343,868 | A | * | 9/1994 | Kurscheidt et al. ........... 600/486 |
| 5,857,975 | A | * | 1/1999 | Golub ........................... 600/485 |
| 5,865,755 | A | * | 2/1999 | Golub ........................... 600/485 |
| 6,331,162 | B1 | * | 12/2001 | Mitchell ....................... 600/485 |
| 6,616,613 | B1 | | 9/2003 | Goodman |
| 6,625,485 | B2 | * | 9/2003 | Levendowski et al. ....... 600/544 |
| 7,074,193 | B2 | * | 7/2006 | Satoh et al. ................... 600/500 |
| 7,708,693 | B2 | * | 5/2010 | Bennett et al. ................ 600/485 |
| 7,815,576 | B2 | | 10/2010 | Wellnhofer |
| 8,380,295 | B2 | * | 2/2013 | Greenhut et al. ............. 600/544 |
| 2002/0082507 | A1 | * | 6/2002 | Kolluri et al. ................. 600/485 |
| 2004/0181157 | A1 | * | 9/2004 | Medero et al. ................ 600/500 |
| 2004/0210145 | A1 | * | 10/2004 | Satoh et al. ................... 600/500 |
| 2004/0230105 | A1 | * | 11/2004 | Geva et al. .................... 600/301 |
| 2005/0004477 | A1 | * | 1/2005 | Friedman et al. ............. 600/485 |
| 2005/0004479 | A1 | * | 1/2005 | Townsend et al. ............ 600/500 |
| 2005/0187481 | A1 | * | 8/2005 | Hatib et al. ................... 600/485 |
| 2006/0122525 | A1 | * | 6/2006 | Shusterman .................. 600/513 |
| 2007/0016087 | A1 | * | 1/2007 | Voith ............................ 600/493 |
| 2007/0100278 | A1 | * | 5/2007 | Frei et al. ....................... 604/66 |
| 2007/0260151 | A1 | * | 11/2007 | Clifford ........................ 600/509 |
| 2008/0294217 | A1 | * | 11/2008 | Lian et al. ....................... 607/28 |
| 2008/0300494 | A1 | * | 12/2008 | Hatib et al. ................... 600/485 |
| 2011/0021928 | A1 | * | 1/2011 | Giovangrandi et al. ...... 600/484 |
| 2012/0109245 | A1 | * | 5/2012 | Hettrick et al. ................. 607/25 |

FOREIGN PATENT DOCUMENTS

WO  00/54650  9/2000

OTHER PUBLICATIONS (PCT/US2010/020616) PCT Notification of Transmittal of the International Search Report and the Written Opinion of the International Searching Authority.

* cited by examiner

*Primary Examiner* — Bill Thomson
*Assistant Examiner* — Bobby Soriano
(74) *Attorney, Agent, or Firm* — Michael C. Soldner

(57) ABSTRACT

A medical device system including a physiological sensor is configured to perform a method for detecting signal artifact in a signal waveform acquired by the sensor. A signal waveform is sensed in a patient using the physiological sensor and a fiducial point associated with the sensed waveform is identified. A point value is established using the fiducial point. Signal artifact is detected in response to the established point value and an established threshold, and at least a portion of the signal waveform is rejected in response to detecting signal artifact.

27 Claims, 9 Drawing Sheets

US 8,702,604 B2

DETECTION OF WAVEFORM ARTIFACT

TECHNICAL FIELD

The disclosure relates generally to implantable medical devices and, in particular, to a method and apparatus for monitoring a physiological signal in a patient and detecting waveform artifact in the signal.

BACKGROUND

Implantable medical devices (IMDs) are available for monitoring physiological signals in a patient. For example, a patient's blood pressure signal may be monitored using a pressure sensor typically mounted along a transvenous lead and advanced to a desired monitoring location. A pressure sensor may be positioned within a ventricular or atrial chamber or along a vein or artery for monitoring for physiological events that influence the blood pressure signal or relate to the hemodynamic status of the patient. Pressure sensor signals contain artifact due to mechanical noise, such as bumping of the pressure sensor against anatomical structures, movement caused by coughing or other respiratory maneuvers, or other movement. This signal artifact may fall within the frequency range of the desired signal properties used for monitoring the patient. As such, artifact removal using conventional filtering or other signal averaging methods may not be effective in removing the artifact without losing desired signal information. Apparatus and methods are needed, therefore, for distinguishing physiological sensor signal waveforms contaminated by artifact from waveforms that do not contain artifact to allow accurate and reliable monitoring of the patient.

DETAILED DESCRIPTION

Figure 1:
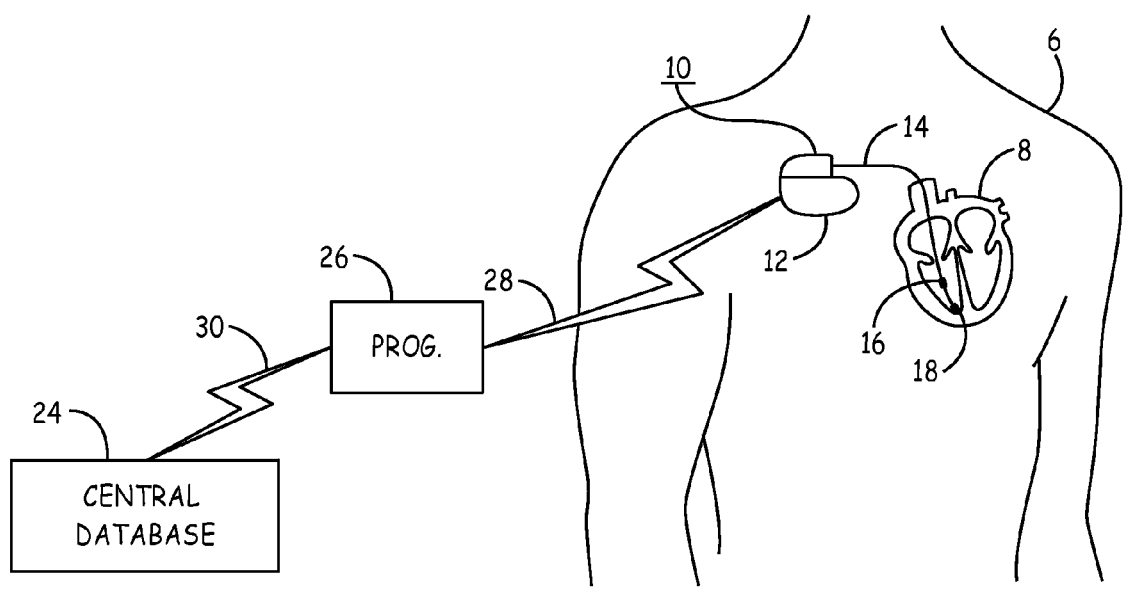
FIG. 1 is a schematic diagram of a patient monitoring system including an implantable medical device (IMD) coupled to a sensor lead positioned within a heart in a patient's body.

In the following description, references are made to illustrative embodiments. It is understood that other embodiments may be utilized without departing from the scope of the disclosure. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic diagram of one illustrative embodiment of a medical device system which may be configured to detect signal artifact according to methods described herein. The medical device system includes an implantable medical device (IMD) 10 coupled to a lead 14 positioned within a heart 8 in a patient's body 6. Lead 14 carries a pressure sensor 16 and one or more electrodes 18.

IMD 10 is at least capable of monitoring physiological signals and may optionally include therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports.

While lead 14 is shown terminated within the right ventricle of the patient's heart, it is recognized that lead 14 may be configured as a transvenous lead that extends into other heart chambers or a vein or artery for positioning a pressure sensor in a desired location. Other illustrative locations for a pressure sensor used to monitor a patient and/or control a therapy include the pulmonary artery, the vena cava, the right atrium, peripheral arteries, larger central arterial locations (such as the aorta) or other locations in the heart or circulation that might not be directly accessed transvenously.

In the illustrative embodiment shown, IMD 10 is provided to monitor a hemodynamic condition of the patient and is capable of sensing and recording intracardiac EGM signals and intracardiac pressure signals and storing cardiac electrical and hemodynamic data. EGM signals are sensed using one or more electrodes 18 carried by lead 14 or using alternative electrodes (not shown) incorporated on the hermetically-sealed housing 12 of IMD 10 or carried by additional electrodes. Housing 12 encloses circuitry (not shown) included in IMD 10 for controlling and performing device functions and processing sensed signals.

Pressure sensor 16 is used for monitoring pressure within the right ventricle. Pressure signals are monitored for determining pressure parameters useful in monitoring a hemodynamic status, diagnosing cardiac dysfunction, and other conditions. The right ventricular intracardiac pressure signal obtained from sensor 16 can be used to derive one or more hemodynamic variables used to monitor patient condition and/or used to control a therapy delivered by the IMD.

In other embodiments, a pressure sensor may be incorporated within the housing of IMD 10 or implemented as a leadless device including a processor and telemetry circuitry. A leadless sensor is capable of acquiring a pressure signal and transmitting pressure data to IMD 10 (or another IMD) or directly to an external device. A leadless sensing device may transmit raw pressure signal data to another device having a processor configured to perform the artifact detection methods described herein and derive pressure parameters from pressure waveforms, or portions thereof, determined to be artifact free. Alternatively, a leadless sensing device may incorporate the processing functionality needed to detect artifact such that pressure waveform data transmitted to another device is artifact free. Information relating to the amount of artifact detected may also be transmitted as an indication of sensor performance.

IMD 10 is capable of bidirectional communication with an external programmer 26 via telemetry link 28. Programmer 26 is used to program the operating mode and various operational parameters of IMD 10 as well as interrogate IMD 10 to retrieve data stored by IMD 10. Stored data may include data related to IMD function determined through automated self-diagnostic tests as well as physiological data acquired by IMD 10 using pressure sensor 16 and electrodes 18.

Programmer 26 is further shown in communication with a central database 24 via communication link 30, which may be a wireless or hardwired link. Programming data and interrogation data may be transmitted via link 30. Central database 24 may be a centralized computer or an Internet-based or other networked database used by a clinician for remote monitoring and management of patient 6. Various methods described herein and executed for detecting signal artifact and computing pressure parameters may be implemented in one or more of the IMD system components shown in FIG. 1, namely in the IMD 10, programmer 26 and/or central database 24, and may include any combination of hardware, firmware and/or software. Programmer 26 may be embodied as a clinic-based programmer having full IMD programming and interrogation functionality or a home-based monitor having interrogation and selected programming functionality and used for remote patient monitoring. It is recognized that other external devices, such as other physiological monitoring devices or other types of programming devices, may be used in conjunction with IMD 10 and incorporate portions of the methods described herein.

Illustrative embodiments described herein utilize a pressure signal acquired using a pressure sensor implantable in a patient's body for monitoring physiological events or conditions. As used herein, the term "pressure signal" includes any pressure signal measured within the body, which may include intracardiac, venous, arterial, or intra-thoracic pressures. Intracardiac pressure signals may be measured in the right or left atrium or in the right or left ventricle. In alternative embodiments, a pressure sensor may be positioned in the pulmonary artery for measuring pulmonary arterial pressure and deriving pressure monitoring parameters.

It should be understood that the methods described herein are not limited to the application of a transvenous blood pressure measurement. Artifact detection methods could be applied to physiological pressure measurements obtained in other body structures or locations, which may or may not be related to blood pressure. A pressure signal may be sensed by a sensor configured and positioned for measuring intracranial pressure, urinary bladder pressure, any intra-cavitary pressure or an intramuscular pressure to illustrate a few examples.

Furthermore, while a pressure sensor and associated pressure signal are referred to in the illustrative embodiments disclosed herein, it is contemplated that the methods described may be implemented in conjunction with any physiological sensor and associated signal that is subject to signal artifact. For example other sensors of mechanical phenomena, such as a motion sensor, a flow sensor, or an acoustical sensor used to monitor a physiological signal, may be subjected to similar types of artifact sources affecting a pressure sensor as described above. Furthermore, it is contemplated that the methods described herein for detecting artifact in a physiological signal may be applied to signals obtained by external devices and are not limited to signals sensed by implantable sensors only. Signals may contain a cyclical cardiac component, a cyclical respiratory component, and/or other physiological waveform changes. Pulsatile or cyclical waveforms or other waveform changes that typically occur in a predictable pattern can be evaluated for the presence of artifact.

Methods described herein allow signal artifact occurring in or near the frequency range of desired physiological signal information to be detected. Decisions made in response to detecting artifact relate to how to use the signal for patient monitoring or other actions, e.g. discarding or retaining a signal waveform or entire series of signal waveforms for use in patient monitoring, repositioning the implanted location of the sensor, or adjusting a therapy controlled at least in part based on the sensed signal.

Figure 2:
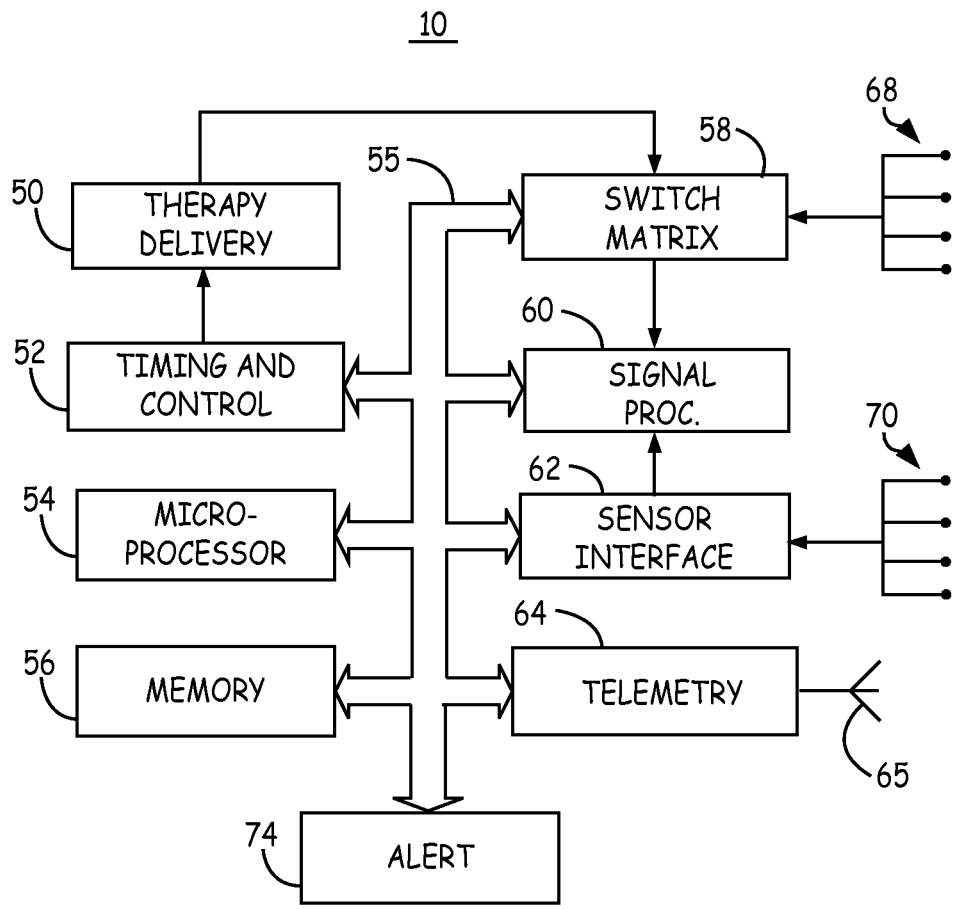
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy under the control of microprocessor 54 in response to determining a need for therapy, e.g., based on sensed physiological signals. In various embodiments, IMD 10 could be a device capable of delivering a medical therapy that is all or in part controlled by a signal sensed by pressure sensor 16 shown in FIG. 1 or another physiological signal. Artifact detection in the physiological signal as described herein may be implemented to improve the quality of the signal or information used by microprocessor 54 to control therapy delivered by module 50. Therapy delivery module 50 may provide drug delivery therapies or electrical stimulation therapies, such as cardiac pacing, cardiac resynchronization therapy, or anti-arrhythmia therapies. Therapies are delivered by module 50 under the control of timing and control circuitry 52.

Therapy delivery module 50 may be coupled to two or more electrode terminals 68 via an optional switch matrix 58 for delivering an electrical stimulation therapy such as cardiac pacing or neurostimulation. Terminals 68 are coupled to connectors providing electrical connection to electrodes incorporated in IMD housing 12 or other lead-based electrodes, such as electrodes 18 carried by lead 14 (shown in FIG. 1).

Electrode terminals 68 may also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. Signal processor 60 receives cardiac signals and includes sense amplifiers and may include other signal conditioning circuitry and an analog-to-digital converter. Cardiac electrical signals received from terminals 68, which may be intracardiac EGM signals, far field EGM signals, or subcutaneous ECG signals, may be used to separate pressure pulse waveforms beat-by-beat in a continuously sensed pressure signal, or waveforms of other sensed signals.

In one embodiment, electrodes coupled to terminals 68 may be used to measure impedance signals, for example, to determine a number of cardiac or vascular impedance vectors that could provide cardiac mechanical signals indicative of cardiac function. Reference is made, for example, to U.S. Pat. No. 5,824,029 (Weijand et al.) and U.S. Pat. No. 6,438,408 (Mulligan, et al.), both of which patents are hereby incorporated herein by reference in their entirety. Physiological impedance signals may be subject to artifact and are another example of physiological signals that the artifact detection methods described herein would also be applicable to for detecting artifact contaminated waveforms.

IMD 10 is additionally coupled to one or more sensors of physiological signals via sensor terminals 70. Physiological sensors may include a pressure sensor 16 as shown in FIG. 1 or other sensors. Physiological sensors may be carried by leads extending from IMD 10, contained inside the IMD, or incorporated in or on the IMD housing 12 or an associated lead connector block.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by microprocessor 54 for detecting physiological events or conditions. In particular, signals from pressure sensor 16 (or other sensors) are processed by signal processor 60 and/or microprocessor 54 for detecting signal artifact and separating waveforms in which artifact is detected from waveforms in which artifact is not detected. An artifact detection algorithm may be stored in memory 56 and executed by microprocessor 54 with input received from sensor terminals 70. In one embodiment, microprocessor 54 is configured to execute a software-implemented artifact detection algorithm. Artifact detection is performed to discriminate between artifact-contaminated signal waveforms that are undesirable for use in patient monitoring or therapy control from waveforms that can reliably be used for determining sensed signal parameters.

The operating system includes associated memory 56 for storing operating algorithms and control parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to pressure parameters, or other sensed physiological signal parameters, by altering a therapy, triggering data storage, enabling other sensors for acquiring physiological data, or triggering alert 74 to generate an alert signal to the patient or a clinician that a serious condition has been detected that may require medical intervention. Data relating to physiological signal processing may be stored in memory 56 for later retrieval.

Signal artifact detection methods may include generating a notification by alert module 74 to notify the patient or a clinician that waveform artifact has reached a significant level, compromising accurate patient monitoring or effective therapy delivery. A notification may be a perceptible signal, e.g. audible or physical, received by the patient or a message transmitted by the IMD using telemetry circuitry 64 and antenna 65. For example, a notification may be generated during a sensor implantation procedure indicating that the signal includes a high degree of artifact and sensor repositioning is recommended.

Figure 3:
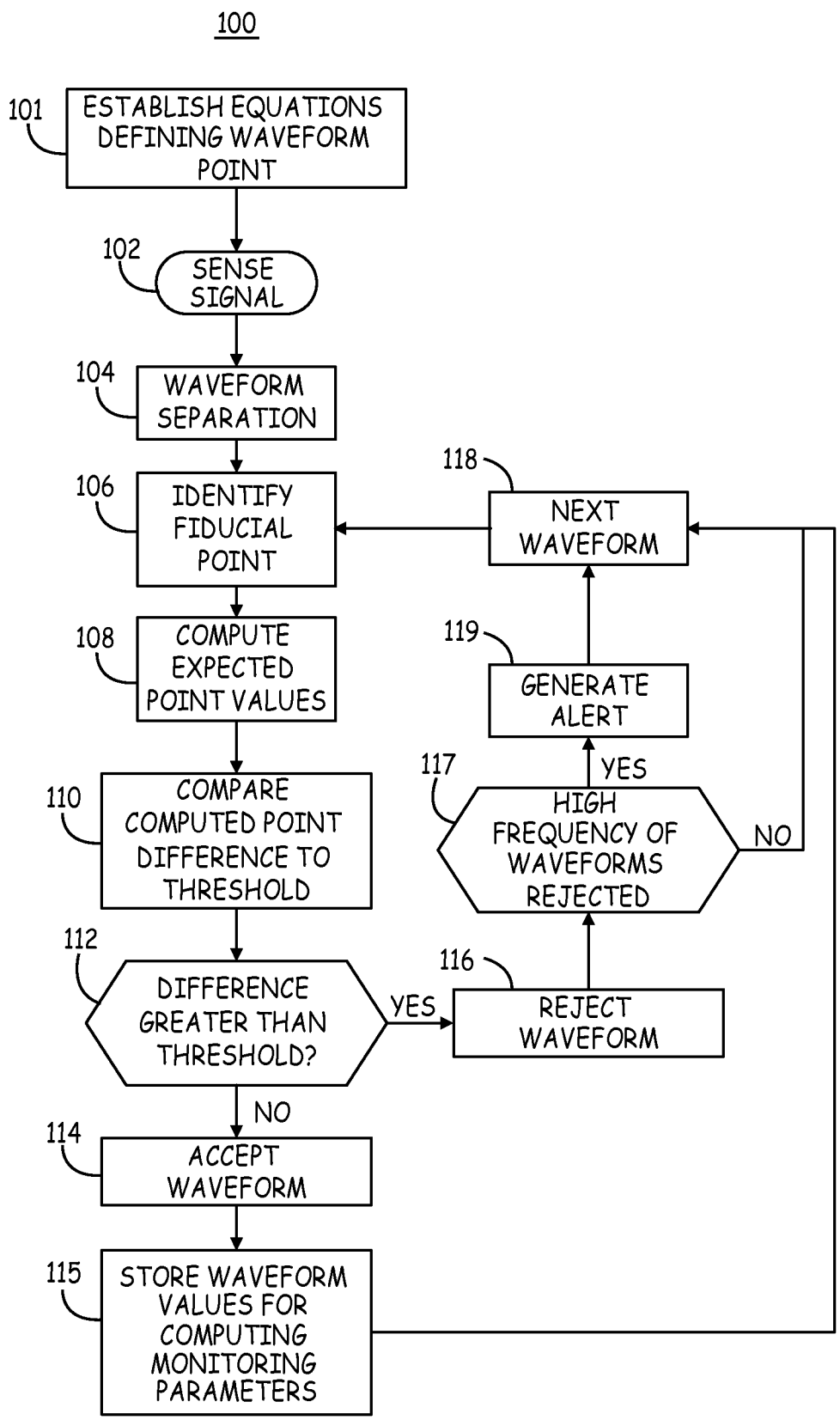
FIG. 3 is a flow chart of one embodiment of a method for detecting signal artifact.

FIG. 3 is a flow chart of one embodiment of a method for detecting signal artifact. At block 101, equations used for artifact detection are established and stored in a memory of the IMD or an external processor for post-processing of physiological signals. At least two equations are established defining an expected point as a function of at least one other fiducial point or associated time interval measured from the signal waveform or a derivative of the waveform. Each equation is used to compute an expected value associated with the waveform based on other features of the waveform. The equations are established based on the waveform morphology that is expected when no artifact is present. When no artifact is present the equations should both yield a similar result of an expected value and represent alternate ways of computing the expected point.

A physiological signal is sensed by an implantable sensor at block 102 and received by a processor for pre-processing including waveform separation at block 104. Typically, a pressure signal is separated into waveform cycles corresponding to cardiac cycles to allow features to be extracted from pressure waveforms on a beat-by-beat basis for computing pressure parameters. In one embodiment, waveform separation performed at block 104 includes identifying endpoints marking the start of each pressure waveform cycle and the end of each cycle corresponding to the start of the next cycle. A waveform endpoint may correspond to a zero-crossing or other threshold crossing, an inflection point, a local maximum or minimum or other identifiable points. Alternatively, a second sensed signal may be used to separate the first sensed signal into waveforms for analysis. For example, a cardiac electrical signal sensed using cardiac electrodes may be used in separating a pressure signal into beat-by-beat waveforms based on intervals measured between sensed cardiac events, such as between consecutively sensed R-waves (RR intervals) or P-waves (PP intervals).

Other cardiac-related signals, which may be a blood flow signal, an accelerometer signal corresponding to cardiac motion, an acoustical sensor sensing heart sounds, or a cardiac impedance signal, may be sensed and separated into waveforms corresponding to cardiac cycles at blocks 102 and 104. In other embodiments, a sensed signal, such as an accelerometer, impedance signal, pressure signal or other physiological signal containing respiratory information may be separated into waveforms corresponding to respiratory cycles.

Waveform separation performed at block 104 includes analog-to-digital conversion at a sampling rate that is selected based on desired signal information. Waveform separation may also include filtering, rectification and other signal conditioning to obtain waveform signals containing the signal information desired for computing signal parameters. Such signal information may still contain artifact falling in or near the desired signal frequency range.

At block 106, a fiducial point associated with a signal waveform is identified. One or more waveform features are measured using the fiducial point. The waveform feature(s) will be used to compute an expected point. A magnitude or time of an expected point may be computed. The expected point is computed at block 108 using the equations established at block 101 and waveform feature(s) measured using the fiducial point. In one embodiment, the expected point is computed using a linear relationship of two points measured on the waveform, using the fiducial point, and occurring earlier in time than the expected point. Two or more values for an expected point are computed using selected features measured from the waveform and a respective number of different equations each defining a value of the expected point.

The fiducial point identified at block 106 is needed for computing the expected point values using the established equations and may or may not be features that have physiological significance. The fiducial point, or features extracted based on the fiducial point, may be used as a monitoring parameter when no artifact is detected. Alternatively, the fiducial point identified at block 106 may not be physiologically meaningful but is useful in detecting artifact present in the waveform using the established equations.

At block 110, a difference between the computed expected point values is compared to a threshold. If the point value difference is greater than an artifact detection threshold, the waveform is rejected as being an artifact-contaminated waveform at block 116. If the difference is not greater than the artifact detection threshold, the waveform is accepted at block 114. The waveform may be stored in digitized format at block 115 for use in later computation of patient monitoring parameters. Alternatively, selected values or features of the waveform may be determined and stored for patient monitoring purposes or for subsequent use in determining and/or adjusting a therapy delivered by the IMD. After determining if the waveform is accepted or rejected, the process returns to block 118 to analyze the next waveform.

In some embodiments, the number or frequency of waveforms being rejected may be tracked. If a threshold frequency or number of waveforms is rejected, as determined at decision block 117, an alert may be generated at block 119 to notify the patient or a clinician of the frequent artifact detection. This notification allows a clinician to adjust programmed parameters, an implant site, or take other action to mitigate the high rate of artifact detection.

Figure 4:
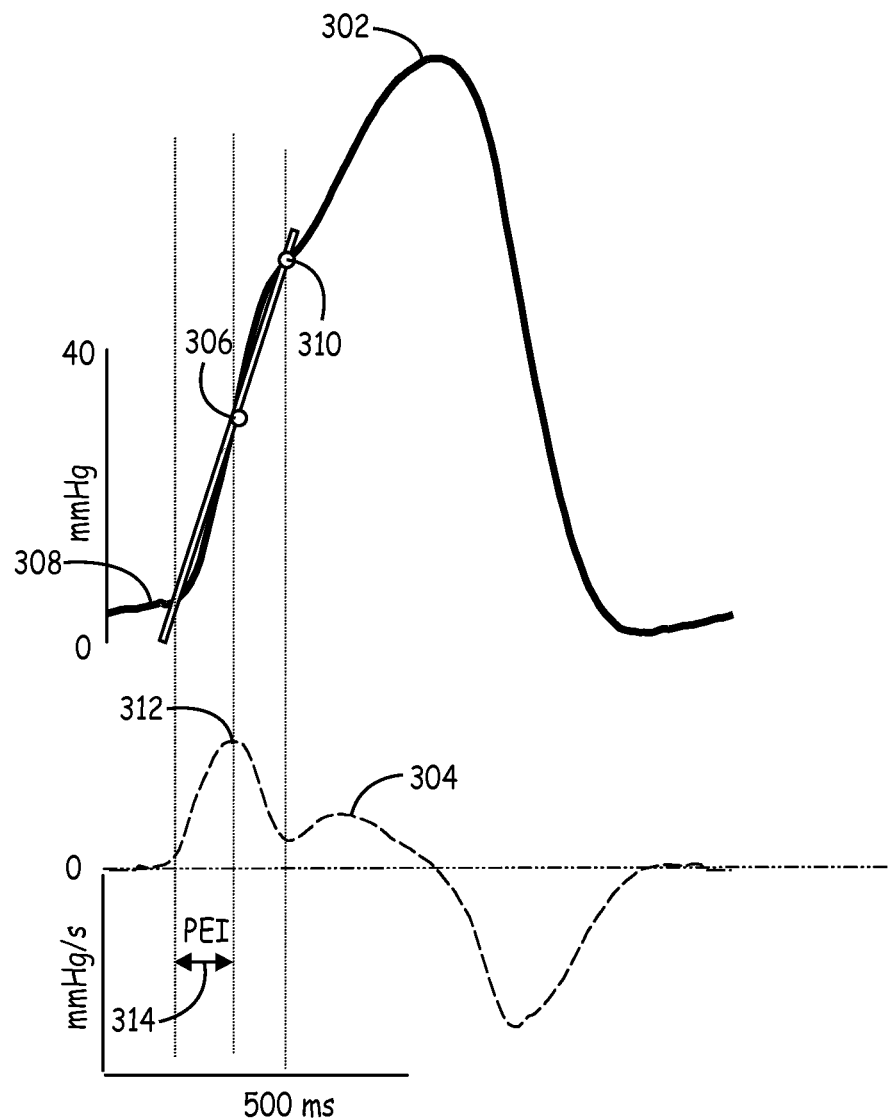
FIG. 4 shows a physiological signal waveform and depicts waveform points used in one embodiment of a method for computing two values of an expected point for detecting artifact.

FIG. 4 shows a physiological signal waveform 302 and depicts waveform points used in one embodiment of a method for computing two values of an expected point for use in detecting artifact. In this illustrative example, the waveform 302 is a right ventricular pressure (RVP) waveform. The first derivative 304 of the waveform is also shown.

Two equations are used to compute an estimated value of an expected point 310 along the waveform based on earlier occurring points along the waveform. The expected point 310 may correspond approximately to the first shoulder of the RVP waveform. In various embodiments, an expected point may be a peak value, an inflection point, a time of a zero crossing, a point corresponding to a maximum or minimum slope, or any other point along the waveform. The expected point, however, does not necessarily fall on the actual waveform and is not compared to a point sampled from the actual waveform for detecting artifact. Rather an artifact detection threshold is applied to computed values of expected points for detecting artifact.

Two equations are defined for computing an estimated value of the expected point 310. As will become apparent, both equations for computing an expected point 310 use a fiducial point determined as the maximum slope, i.e. the maximum peak 312 of the waveform first derivative 304. A first equation is a function of earlier occurring points 308 and 306 along the waveform 302. In one embodiment, a linear function defines the expected point as P=c(X−B)+B, wherein X and B are the previously occurring points measured along the waveform P is assumed to be a multiple of the difference between the points added to the first point.

In the illustrated example of FIG. 4, the baseline point 308 corresponds to right ventricular diastolic pressure (RVDP). The baseline 308 may be measured as an average value of the signal between waveforms or a signal amplitude measured at or just before detecting a waveform onset. For example, baseline 308 may be the value of the RVP waveform at the time that dP/dt 304 begins to rise above 0. The second point 306 occurring earlier than the expected point 310 corresponds to the magnitude of the waveform 302 at the time of the maximum slope, i.e. at maximum first derivative 312.

In one embodiment, the first equation for computing a value for an expected point W1 associated with a waveform "W" of a sensed physiological signal, can be given generally as:

$$W1 = c \times (W_{dW/dtmax} - \text{baseline}) + \text{baseline}$$

wherein c is a constant, and $W_{dW/dtmax}$ is the magnitude of a point along the sensed waveform at the time of the maximum first derivative, $dW/dt_{max}$, of the waveform.

More specifically for the given example corresponding to a RVP signal:

$$P1 = 2 \times (EPAD - RVDP) + RVDP$$

wherein EPAD is the estimated pulmonary artery diastolic pressure 306 determined as the amplitude of the RVP waveform 302 at the fiducial point $dP/dt_{max}$ 312. RVDP is the baseline 308 of the RVP waveform.

The constant c is set to a value of 2 in the above equation. A different constant may be chosen to optimize the estimated value of point 310 based on typical relationships between EPAD, RVDP, and the peak of the RVP waveform when artifact is not present. The constant c may be tailored to individual patients. In alternative embodiments, the constant c may correspond to a value measured from the first derivative 304. For example, the constant c may correspond to the magnitude of the peak slope 312 or a proportion of the peak slope 312.

A second equation for estimating a second value of the expected point may be written as a function of a time interval measured using the peak slope as a fiducial point for defining the time interval. A second equation may be written in general terms as $$W2 = (b \times (dW/dt_{max}) \times (t_{dW/dtmax})) + W_{dW/dtmax}$$

wherein b is a constant, $dW/dt_{max}$ is the maximum of the first derivative of the waveform W or the peak slope, $t_{dW/dtmax}$ is a time interval extending from the waveform onset to the peak slope, and $W_{dW/dtmax}$ is the amplitude of the waveform at the time of the peak slope. In this case, the expected point is computed from a starting point at which $dW/dt_{max}$ occurs and adding the product of a proportion of the maximum slope, $b \times dW/dt_{max}$, and the time interval to reach $dW/dt_{max}$.

For the example shown in FIG. 4 where the waveform 302 is RVP, the second equation for computing a second value P2 of an expected point using the maximum slope fiducial point can be expressed more specifically as:

$$P2 = (0.5 \times (dP/dt\max) \times PEI)) + EPAD$$

wherein EPAD is the estimated pulmonary artery diastolic pressure 306 as described above and PEI is the pre-ejection interval 314 corresponding to the interval of time between the onset 308 of the RVP waveform and the time of $dP/dt_{max}$ 312.

Both of the first and second values of the expected point are computed using respective equations and the maximum slope as a fiducial point needed for measuring terms used in the respective equations. Both equations are expected to provide a good estimate of the amplitude of the waveform 302 at point 310 when no artifact is present in the early phase of the waveform. As such, when no artifact is present the difference between P1 and P2 given by the above equations is expected to be relatively small. If artifact is present, the difference between P1 and P2 will be larger due to an unexpected morphology of the waveform.

Accordingly, an artifact detection threshold can be established for detecting artifact occurring in the waveform 302 based on the difference of P1 and P2. In the given example, the equations for P1 and P2 are written to estimate the value of an expected point 310 occurring during the early phase of the waveform 302. In the given example, the artifact will be detected during the systolic phase of the cardiac cycle. In other embodiments, two or more equations may be written to predict a value of an expected waveform point any where along the waveform. The equations may be linear or non-linear functions of earlier occurring points and/or time intervals measured from the waveform or later occurring points and/or time intervals determined using a fiducial point associated with the waveform.

The computed values P1 and P2 will be substantially equal for the artifact-free waveform shown. P1 and P2 are not measured from the waveform directly or compared directly to a waveform measurement. Rather P1 and P2 are computed values of an expected point based on measurements of the waveform taken at different points in time than the expected point. The method to detect artifact therefore predicts a value of an expected point, using at least two different equations and corresponding waveform measurements taken at different time points than the expected point, and looks for convergence of the expected values as an indication of a normal waveform morphology. Comparison of an expected point value computed using the established equations and an actual point on the waveform is not performed in the method described in conjunction with FIGS. 3-4, but such a comparison could be performed in other embodiments.

Figure 5:
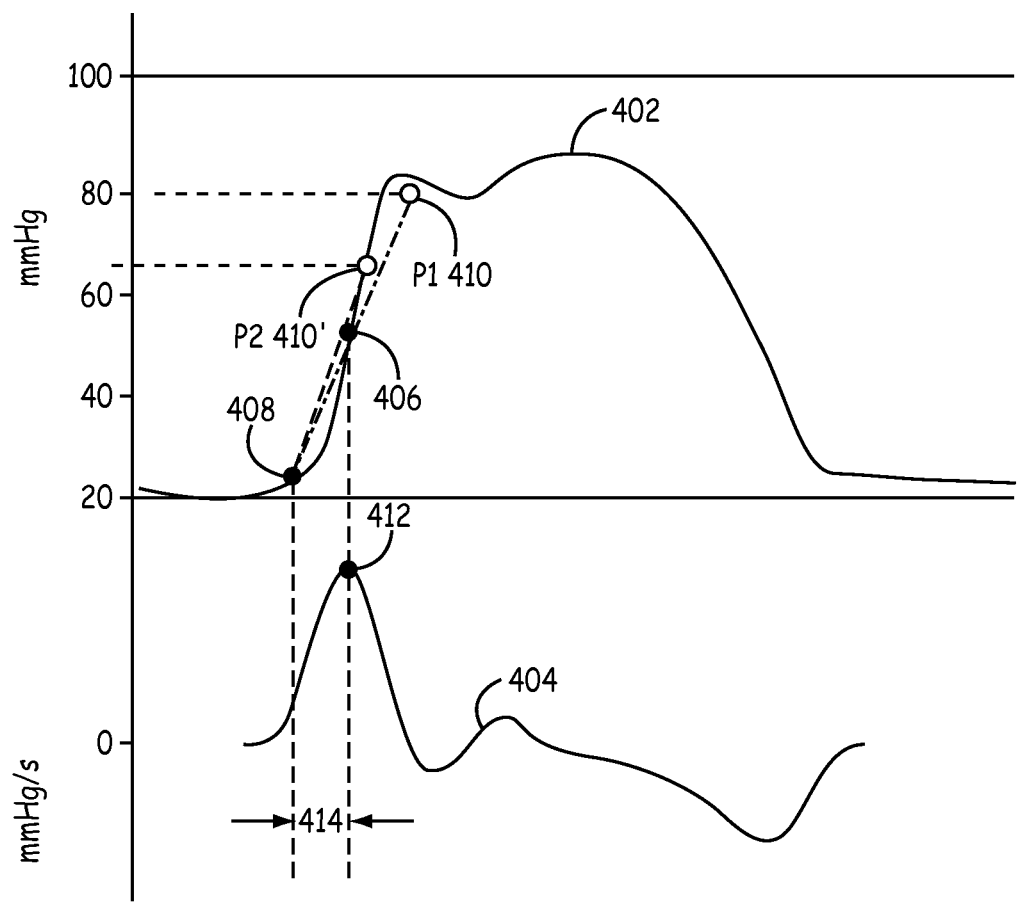
FIG. 5 shows a right ventricular pressure waveform contaminated by artifact in the early phase of the waveform and how waveform points described in conjunction with FIG. 4 are used in one embodiment to detect the presence of the artifact.

FIG. 5 shows a right ventricular pressure waveform 402 contaminated by artifact in the early phase of the waveform. Waveform features as described in conjunction with FIG. 4 are determined using the maximum slope as a fiducial point. The waveform features are used with established equations to compute expected points for detecting the presence of this early artifact. According to the first equation described above, a first value of an expected point P1 410 is computed as the sum of the baseline (RVDP 408) and twice the difference between EPAD 406 and RVDP 408. P1 410 is approximately 80 mmHg.

The second equation described above for computing a second value of an expected point P2 410' results in a value of approximately 65 mmHg based on the sum of EPAD 406 and the product of half of $dP/dt_{max}$ 412 and PEI 414. The difference between P1 410 and P2 410' is approximately 15 mmHg. Both values of the expected point are computed using a fiducial point associated with the sensed waveform 402, corresponding to the maximum slope 412 of the waveform.

In one embodiment, an artifact detection threshold is approximately 10 mmHg. Since the difference between P1 410 and P2 410' is greater than 10 mmHg, artifact is detected in the early phase of the RVP waveform 402. Any parameters derived using the early phase of the RVP waveform 402 for monitoring the patient or controlling a therapy would be rejected. For example, if EPAD is being monitored in a heart failure patient, waveform 402 would be rejected and not used for measuring EPAD for purposes of determining a heart failure status.

Figure 6:
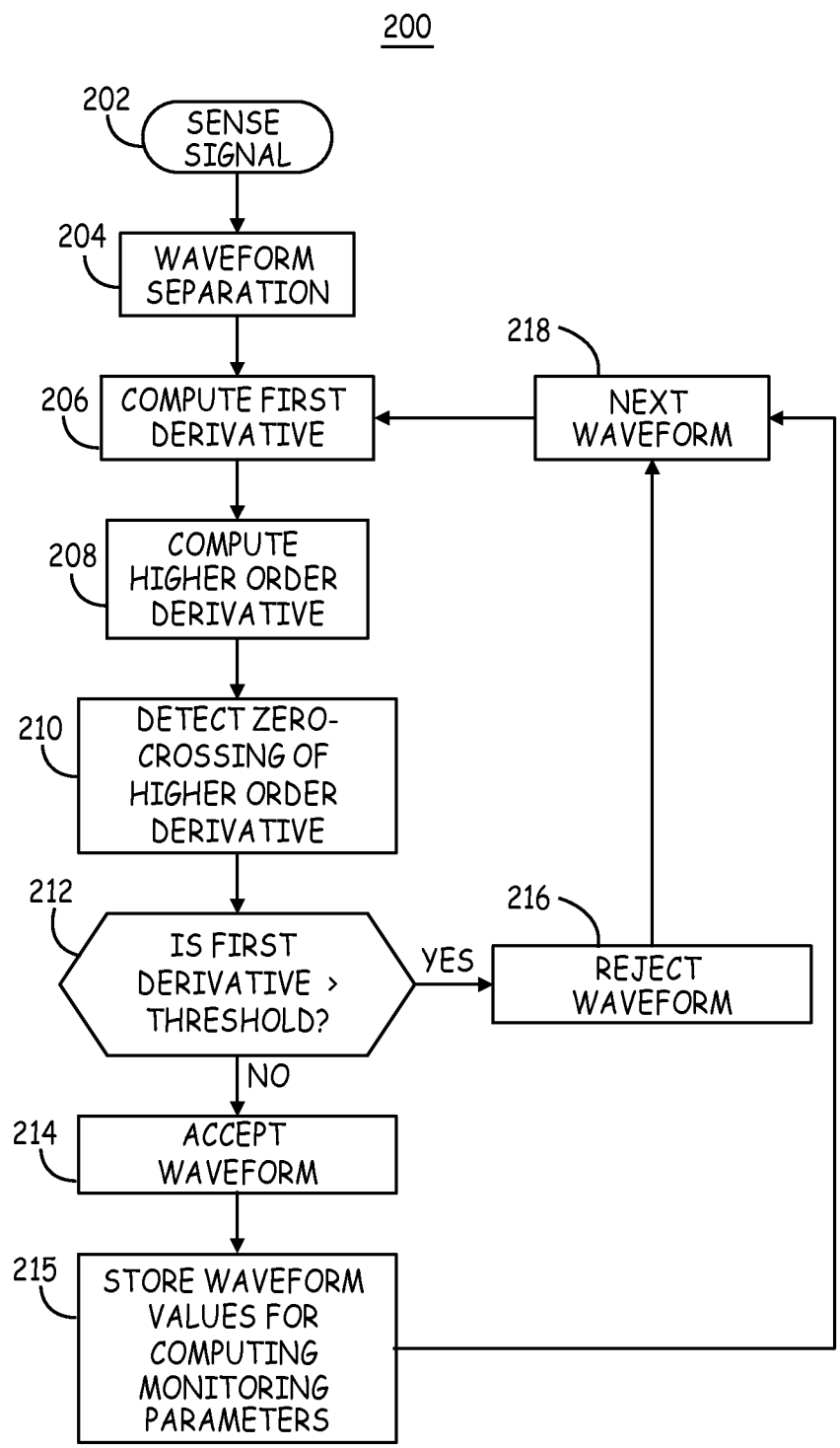
FIG. 6 is a flow chart of an alternative method for determining if a physiological signal waveform is contaminated by artifact.

FIG. 6 is a flow chart 200 of an alternative method for determining if a physiological signal waveform is contaminated by artifact. At block 202, a physiological signal is sensed and separated into cyclic waveforms at block 204 as described previously. At block 206, the first derivative of the waveform is computed. The first derivative provides information about how the slope of the waveform is changing over time. A higher order derivative is computed at block 208. In one embodiment, the fourth derivative is computed at block 208.

A zero-crossing of the higher order derivative, which is preceding the minimum first derivative of the waveform in one embodiment, is identified at block 210. The value of the first derivative at the zero-crossing of the higher-order derivative is examined at block 212. If the first derivative at the time of the higher-order derivative zero crossing is greater than an artifact detection threshold, as determined at block 212, the waveform is rejected at block 216. If not, the waveform is accepted at block 214. The waveform is used for patient monitoring purposes at block 215 as described previously. After either accepting or rejecting the waveform based on the analysis of the first derivative value at a time point selected based on a higher order derivative zero-crossing, analysis of the next waveform begins by advancing to block 218. As described previously and shown in FIG. 3, the number or frequency of rejected waveforms may be tracked to allow user notification when a high rate of artifact detection is occurring.

Generally, the higher order derivative zero-crossing is used to approximate a selected time point along the waveform. As such, the higher-order derivative zero crossing is identified as a fiducial point used for detecting artifact. The value of the first order derivative indicates whether the waveform is increasing or decreasing at the selected time point. This information can be used as an indicator of the presence of artifact as will be further described below based on knowledge of the expected artifact-free waveform morphology. A point value for detecting threshold is determined as the value of the first derivative of the waveform at the time of the zero crossing of the higher order derivative. A threshold applied to the established point value corresponds to whether the waveform morphology is normally increasing or decreasing or relatively flat at the time of the zero crossing when artifact is not present.

Figure 7:
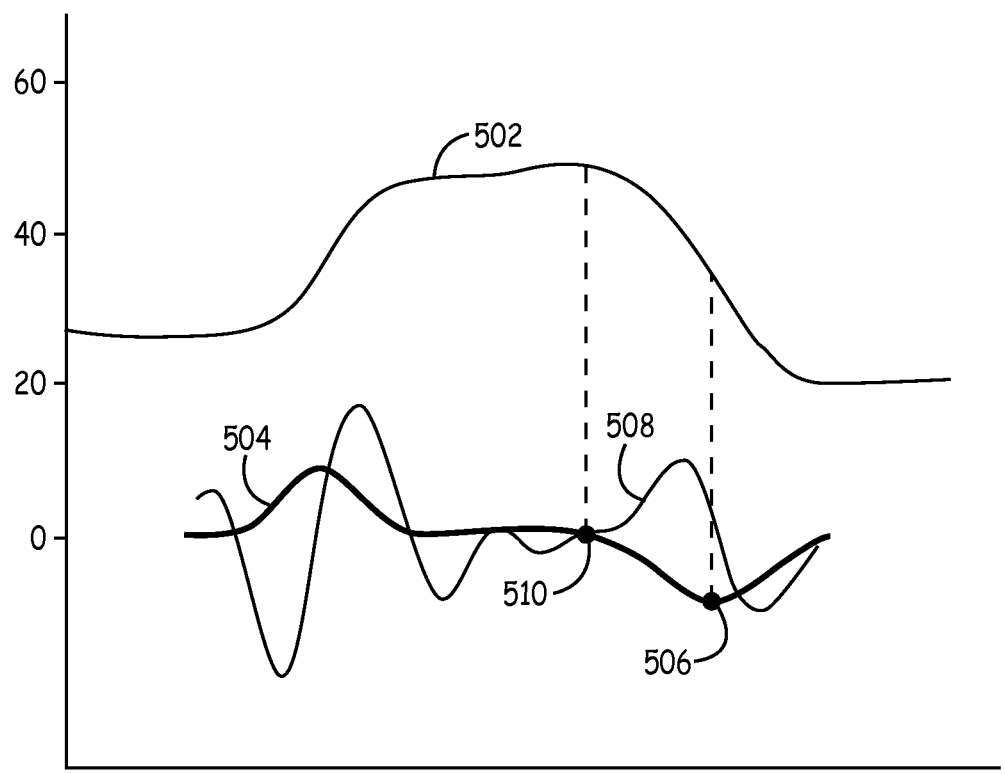
FIG. 7 shows a physiological waveform and depicts a first derivative and higher order derivative of the waveform used in another embodiment of a method for detecting signal artifact.

FIG. 7 is a physiological waveform 502 and depicts a first derivative and higher order derivative of the waveform used in another embodiment of a method for detecting signal artifact. Waveform 502 is a RVP waveform. The first derivative 504 and the fourth derivative 508 of the waveform 502 are shown. In one embodiment, the waveform 502 is examined for artifact in the late phase of the waveform by determining the magnitude of dP/dt 504 at a zero-crossing 510 of $d^4P/dt^4$. The zero-crossing 510 is identified as a fiducial point for detecting artifact. The zero-crossing 510 is identified as the most recently occurring negative-to-positive going zero-crossing preceding the minimum dP/dt 506 of the waveform.

When no artifact is present, dP/dt is expected to be near zero at the zero-crossing 510, as can be seen in FIG. 7. The pressure is at or near the peak pressure or beginning to fall and is not expected to be rising when no artifact is present. The value of dP/dt 508 at the zero-crossing 510 of the higher order derivative can be compared to an artifact detection threshold. If dP/dt 508 is still positive or above a predefined threshold at the zero-crossing, pressure is still rising indicating a presence of artifact. In other words, an expected behavior of the RVP waveform when no artifact is present is a near zero or negative dP/dt 508 at the time of the most recent negative-to positive zero crossing of the fourth derivative preceding the minimum dP/dt 506.

Figure 8:
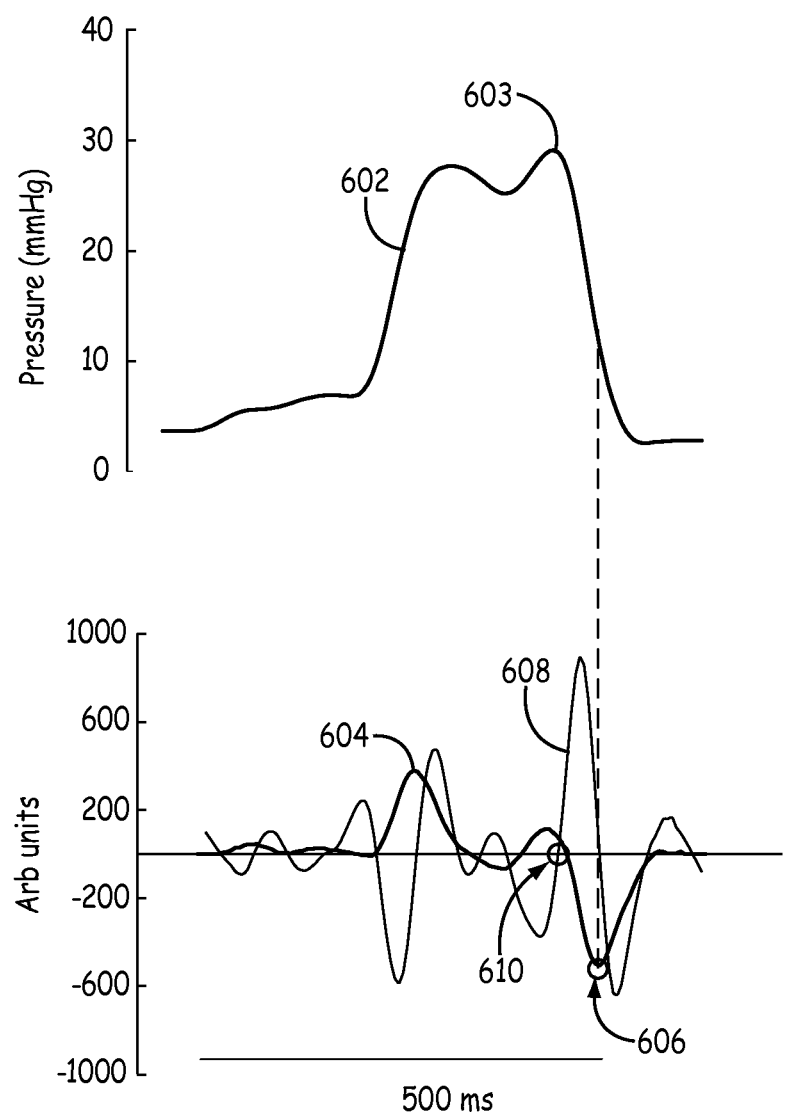
FIG. 8 is a right ventricular pressure waveform containing late artifact and depicts points along the first derivative and the higher order derivative of the waveform that are used in detecting the presence of artifact.

FIG. 8 is a RVP waveform 602 containing late artifact as observed by the large second peak 603. FIG. 8 depicts fiducial points identified along the first derivative of the waveform and the higher order derivative of the waveform that are used in detecting the presence of this late artifact. The most recent positive-to-negative zero crossing 610 of the fourth derivative 608 preceding minimum dP/dt 606 is identified. The value of dP/dt at zero crossing 610 is compared to an artifact detection threshold. In one embodiment, the threshold is zero. Since dP/dt is still positive (i.e. greater than zero), RVP is still increasing at the time point of zero-crossing 610. This increasing RVP is caused by the late artifact. Thus artifact is detected based on the positive value of dP/dt at zero-crossing 610.

Figure 9:
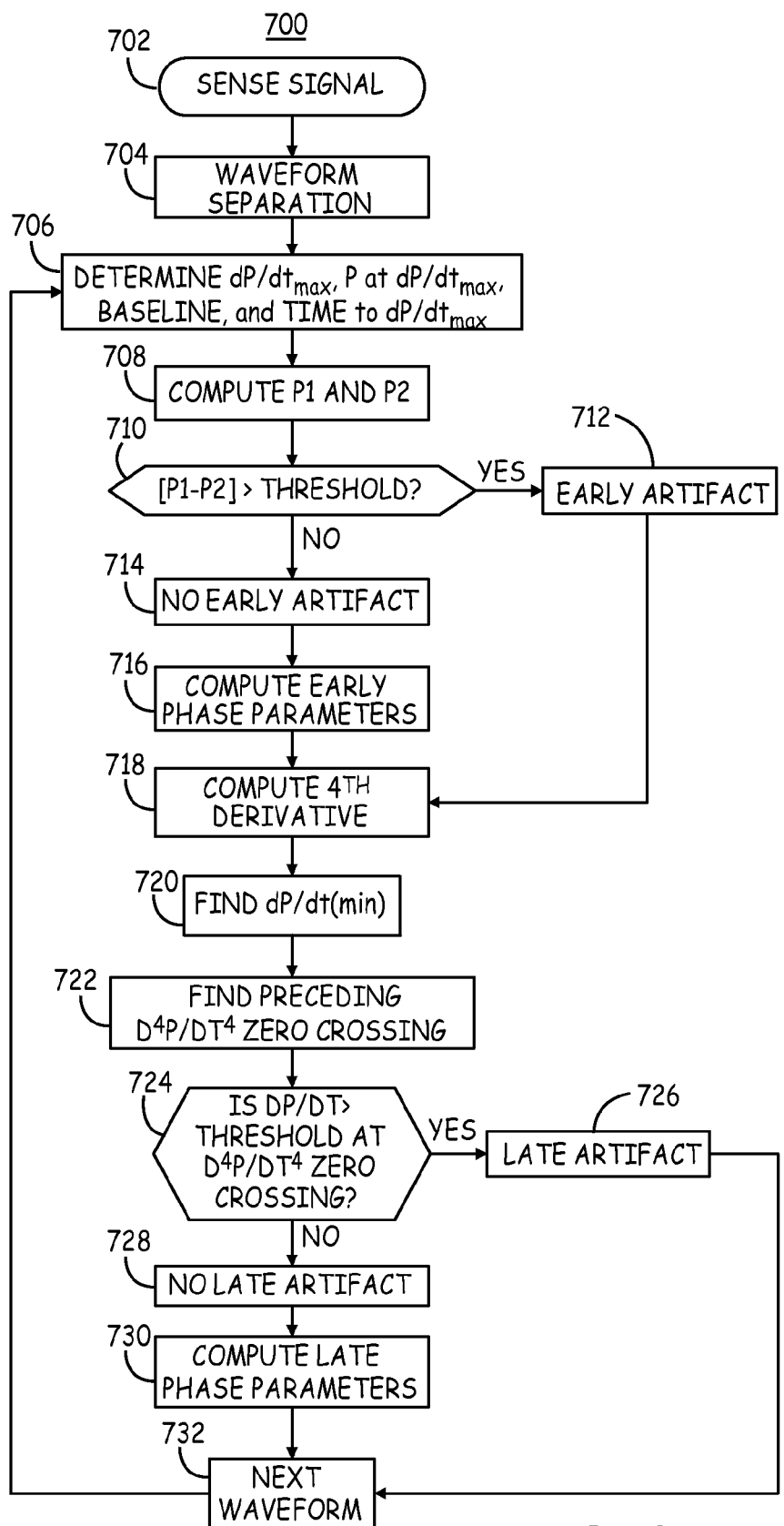
FIG. 9 is a flow chart of a method for detecting early and late artifact in a physiological waveform.

FIG. 9 is a flow chart 700 of a method for detecting early and late artifact in a physiological waveform. In the foregoing examples, and as will be described in conjunction with flow chart 700, detection of early artifact in a pressure waveform may be achieved using two equations defined to compute values of an expected point along the waveform and late artifact detection may be achieved using the value of a first derivative of a pressure waveform at a selected zero-crossing of a higher order derivative. It is recognized, however, that any of the methods described herein may generally be used, alone or in combination, to detect artifact along any portion of a physiological signal waveform. Slope and intercept values in established equations, fiducial points used to measure waveform features, and/or artifact detection thresholds may be adapted as necessary based on expected waveform morphology to appropriately detect artifact along any portion of a physiological waveform.

At block 702, a physiological signal is sensed, and it is separated into cyclical waveforms at block 704 as described previously. In one embodiment, the waveform is a pressure waveform and the equations described above are used to detect early artifact in the waveform (i.e. artifact occurring substantially earlier than the pressure peak). Features of the waveform and/or a derivative of the waveform are determined at block 706 as needed for computing values of an expected point along the waveform using previously established equations.

As described above, a maximum dP/dt is determined as a fiducial point and used to measure a time interval from the onset of the waveform to the maximum dP/dt and the magnitude of the waveform at dP/dt max. The waveform baseline and the measured features are determined as needed for computing point values P1 and P2 using two different equations. When the waveform is a RVP waveform, the features determined from the waveform include RVDP, EPAD and PEI.

At block 708, P1 and P2 are computed. P1 and P2 are two different values of an expected point occurring along the waveform computed using earlier occurring waveform features using the maximum slope as a fiducial point. The earlier occurring waveform features may be those listed above or any other magnitude or time interval associated with the waveform.

At block 710, the absolute difference between the computed P1 and P2 values is compared to an artifact detection threshold. If the difference is greater than the threshold, early artifact is detected at block 712. No further analysis of the early portion of the waveform is performed for use in patient monitoring or therapy control.

If the difference between the computed P1 and P2 values is less than the threshold, no artifact is detected at block 714. The waveform is used at block 716 to compute pressure parameters that are derived from the early portion of the waveform, e.g. EPAD and PEI, for use in patient monitoring and/or therapy control.

Beginning at block 718, the waveform is examined for late artifact. The fourth derivative is computed at block 718. The minimum dP/dt is found at block 720. The most recent negative-to-positive zero crossing of the fourth derivative that precedes dP/dt min is identified at block 722 as a fiducial point used for establishing a point value for artifact detection. The point value is the value of dP/dt at the zero-crossing, which is compared to an artifact detection threshold at block 724. If dP/dt is greater than the threshold, late artifact is detected at block 726. The waveform is not used for computing monitoring or therapy control parameters that are determined using waveform features occurring in the late phase, e.g. $dP/dt_{min}$ and a systolic time index.

If no artifact is present in the late phase of the waveform at block 728 based on dP/dt at the zero crossing of the higher order derivative, pressure monitoring or therapy control parameters that are determined using features of the waveform during the late phase are computed at block 730.

At block 732 the monitoring process advances to the next waveform. The method shown by the flow chart 700 allows some pressure parameters to be computed using portions of the waveform determined to be artifact free while other artifact-contaminated portions of the waveform are discarded and not used for patient monitoring or therapy control. In other embodiments, if any portion of the waveform is found to be contaminated, the entire waveform may be rejected. It is recognized that in some embodiments, monitoring or therapy control parameters may be computed using features determined from both an early and late phase of a physiological waveform. Such parameters may be computed after determining the waveform is artifact free in both the early and late phases. Furthermore it is recognized that while methods described herein refer to artifact detection in an early phase and a late phase, the detection methods may be applied to multiple phases of a waveform including one or more early, mid- and late phases.

Thus, an implantable medical device system and associated method for detecting physiological signal artifact have been presented in the foregoing description with reference to specific embodiments. It is appreciated that various modifications to the referenced embodiments may be made without departing from the scope of the disclosure as set forth in the following claims.

The invention claimed is:

1. Method for detecting signal artifact in a physiological signal waveform acquired by a physiological sensor, the method comprising:
sensing a signal waveform in a patient using the physiological sensor;
identifying a fiducial point from the sensed waveform;
establishing an expected value of an expected point of the sensed waveform using the fiducial point;
establishing an artifact detection threshold;
detecting signal artifact in the sensed waveform in response to the expected point value and the established threshold; and
rejecting at least a portion of the signal waveform in response to detecting signal artifact.

2. The method of claim 1, further comprising:
establishing a first equation for computing a first value of the expected point;
establishing a second equation for computing a second value of the expected point;
wherein the threshold is established as a threshold difference between the first and second values;
computing the first and second values of the point using the established equations and the fiducial point; and
detecting signal artifact in response to a difference between the first and second values being greater than the threshold.

3. The method of claim 2, wherein the fiducial point occurs at a time other than a time of the expected point.

4. The method of claim 2, wherein the fiducial point is associated with a maximum slope of the signal waveform.

5. The method of claim 4, wherein the first value is computed using a proportion of a magnitude of the waveform measured at the maximum slope of the waveform.

6. The method of claim 4, wherein the second equation is a function of an earlier occurring time interval having an endpoint associated with the maximum slope of the signal waveform.

7. The method of claim 4, wherein the second value is computed using a proportion of a product of the maximum positive slope and a time interval measured between an onset of the waveform and the maximum positive slope of the waveform.

8. The method of claim 1, wherein identifying the fiducial point comprises:
   determining a first derivative of the waveform;
   determining a higher order derivative of the waveform; and
   identifying a zero-crossing point of the higher order derivative.

9. The method of claim 8, wherein the expected point corresponds to an amplitude of the first derivative of the waveform at the zero-crossing point.

10. The method of claim 8, wherein identifying the zero-crossing point comprises identifying a minimum value of the first derivative and identifying the most recently occurring zero-crossing of the higher order derivative preceding the minimum value of the first derivative.

11. The method of claim 8, wherein the higher order derivative is a fourth order derivative.

12. The method of claim 1, wherein the sensed signal waveform is a pressure waveform.

13. The method of claim 1, further comprising counting a number of rejected waveforms and generating an alert signal when a threshold number of waveforms are rejected.

14. A medical device system for monitoring a physiological signal in a patient and detecting artifact in the physiological signal, the system comprising:
   a sensor for sensing a physiological signal waveform; and
   a processor configured to receive the sensed signal waveform, identify a fiducial point from the sensed waveform, establish an expected value of an expected point of the sensed waveform using the fiducial point, establish an artifact detection threshold, detect signal artifact in the sensed waveform in response to the expected point value and the established threshold, and reject at least a portion of the signal waveform in response to detecting the signal artifact.

15. The system of claim 14, wherein the processor is configured to establish a first value of the expected point using a first equation and the fiducial point and a second value of the expected point using a second equation and the fiducial point, and detect signal artifact in response to a difference between the first and second values being greater than the threshold.

16. The system of claim 14, wherein the fiducial point occurs at a time other than a time of the expected point.

17. The system of claim 15, wherein the fiducial point is associated with a maximum slope of the signal waveform.

18. The system of claim 17, wherein the first value is computed using a proportion of a magnitude of the waveform measured at the maximum slope of the waveform.

19. The system of claim 17, wherein the second equation is a function of an earlier occurring time interval having an endpoint associated with the maximum slope of the signal waveform.

20. The system of claim 17, wherein the second value is computed using a proportion of a product of the maximum positive slope and a time interval measured between an onset of the waveform and the maximum positive slope of the waveform.

21. The system of claim 14, wherein identifying the fiducial point comprises:
   determining a first derivative of the waveform;
   determining a higher order derivative of the waveform; and
   identifying a zero-crossing point of the higher order derivative.

22. The system of claim 21, wherein the expected point value corresponds to an amplitude of the first derivative of the waveform at the zero-crossing point.

23. The system of claim 21, wherein identifying the zero-crossing point comprises identifying a minimum value of the first derivative and identifying the most recently occurring zero-crossing of the higher order derivative preceding the minimum value of the first derivative.

24. The system of claim 21, wherein the higher order derivative is a fourth order derivative.

25. The system of claim 14, wherein the sensed signal waveform is a pressure waveform.

26. The system of claim 14, further comprising an alert module and wherein the processor is further configured to count a number of rejected waveforms and cause the alert module to generate an alert signal when a threshold number of waveforms is rejected.

27. A non-transitory computer-readable medium storing a set of instructions which cause a medical device system comprising a physiological sensor to perform a method, the method comprising:
   sensing a signal waveform in a patient using the physiological sensor;
   identifying a fiducial point from the sensed waveform;
   establishing an expected point value of the sensed waveform using the fiducial point;
   establishing an artifact detection threshold;
   detecting signal artifact in the sensed waveform in response to the established expected point value and the established threshold; and
   rejecting at least a portion of the signal waveform in response to detecting signal artifact.

* * * * *